United States Patent
Dolgos et al.

(10) Patent No.: US 9,703,926 B2
(45) Date of Patent: Jul. 11, 2017

(54) METHOD FOR CUSTOMIZATION OF USER INTERFACE OF A MEDICAL APPARATUS FOR EXTRACORPORAL BLOOD TREATMENT; MEDICAL APPARATUS FOR EXTRACORPORAL BLOOD TREATMENT

(71) Applicant: B. Braun Avitum AG, Melsungen (DE)

(72) Inventors: Sandor Dolgos, Szentendre (HU);
Robert G. Schin, Budapest (HU);
Peter Szamko, God (HU); Gyorgy Bogatin, Budapest (HU)

(73) Assignee: B. BRAUN AVITUM AG, Melsungen (DE)

( * ) Notice: Subject to any disclaimer, the term of this patent is extended or adjusted under 35 U.S.C. 154(b) by 393 days.

(21) Appl. No.: 13/870,375

(22) Filed: Apr. 25, 2013

(65) Prior Publication Data

US 2013/0298062 A1  Nov. 7, 2013

(30) Foreign Application Priority Data

May 3, 2012 (EP) ..................................... 12166672

(51) Int. Cl.
*G06F 3/048* (2013.01)
*G06F 19/00* (2011.01)
(Continued)

(52) U.S. Cl.
CPC ............ *G06F 19/32* (2013.01); *G06F 3/0488* (2013.01); *G06F 3/04847* (2013.01);
(Continued)

(58) Field of Classification Search
None
See application file for complete search history.

(56) References Cited

U.S. PATENT DOCUMENTS 5,858,239 A * 1/1999 Kenley ............... A61M 1/3627
210/143
6,005,577 A * 12/1999 Breitlow ............... G06F 3/0489
700/83
(Continued)

FOREIGN PATENT DOCUMENTS

CN  101247840  8/2008
CN  101341489  1/2009
(Continued)

OTHER PUBLICATIONS

European Search Report for EP 12 16 6672 dated Oct. 12, 2012.
(Continued)

*Primary Examiner* — Mahelet Shiberou
(74) *Attorney, Agent, or Firm* — RatnerPrestia

(57) ABSTRACT

Methods for customization of a user interface of a microprocessor controlled medical apparatus for extracorporal blood treatment are disclosed, whereby the medical apparatus comprises a software component driving the user interface on a touch screen of the medical apparatus, and the software component has a technical support and maintenance mode and a treatment mode. At least one target window is displayed on the touch screen during therapy in the treatment mode, and such target window shows at least data regarding measured and/or set values of the therapy, whereby at least the appearance of one target window is modified by a customization procedure that is performed within the target window in the treatment mode. The invention further relates to a medical apparatus for extracorporal blood treatment that uses the method.

11 Claims, 3 Drawing Sheets

(51) Int. Cl.
    *G06F 3/0488*     (2013.01)
    *G06F 3/0484*     (2013.01)
    *A61M 1/16*     (2006.01)

(52) U.S. Cl.
    CPC .......... *G06F 19/3481* (2013.01); *A61M 1/16* (2013.01); *A61M 2205/505* (2013.01); *A61M 2205/52* (2013.01)

(56) References Cited

U.S. PATENT DOCUMENTS

| | | |
|---|---|---|
| 7,988,850 B2 | 8/2011 | Roncadi et al. |
| 8,075,509 B2 | 12/2011 | Molducci et al. |
| 8,529,485 B2 | 9/2013 | Bock et al. |
| 2002/0116226 A1* | 8/2002 | Auer ................ G06F 19/321 705/3 |
| 2007/0138069 A1* | 6/2007 | Roncadi .............. A61M 1/16 210/96.2 |
| 2008/0134071 A1 | 6/2008 | Keohane et al. |
| 2008/0249377 A1* | 10/2008 | Molducci ............ A61M 1/16 600/301 |
| 2008/0281168 A1* | 11/2008 | Gibson ............ A61B 5/0205 600/301 |
| 2011/0004071 A1 | 1/2011 | Faiola et al. |
| 2011/0029865 A1* | 2/2011 | Gilland ............ G06F 19/3406 715/702 |
| 2013/0125052 A1* | 5/2013 | Baird .................. G06F 3/0482 715/810 |

FOREIGN PATENT DOCUMENTS

| | | |
|---|---|---|
| CN | 101505813 | 8/2009 |
| CN | 101860698 | 10/2010 |
| WO | WO98/29790 | 7/1998 |

OTHER PUBLICATIONS

Chinese Office Action (translation) for CN201310160879.1 dated Dec. 26, 2016.
Chinese Search Report (translation) for CN201310160879.1 dated Dec. 16, 2016.

* cited by examiner

METHOD FOR CUSTOMIZATION OF USER INTERFACE OF A MEDICAL APPARATUS FOR EXTRACORPORAL BLOOD TREATMENT; MEDICAL APPARATUS FOR EXTRACORPORAL BLOOD TREATMENT

CROSS REFERENCE TO RELATED APPLICATIONS

This application claims priority to European Application No. EP 12 166 672.1 filed May 3, 2012, the contents of such application being incorporated by reference herein.

FIELD OF THE INVENTION

The invention relates to a method for customization of a user interface of a microprocessor controlled medical apparatus for extracorporal blood treatment, whereby the medical apparatus comprises a software component driving the user interface on a touch screen of the medical apparatus, and the software component has a technical support and maintenance mode and a treatment mode.

The invention further relates to a medical apparatus for extracorporal blood treatment that uses this method.

BACKGROUND OF THE INVENTION

Modern medical apparatuses are often controlled by a microprocessor that, for example, operates pumps, reads sensors and communicates with an operator via a user interface like a monitor, keypad and/or touchscreen. This user interface can make use of text, pictograms and/or graphical icons to guide an operator through the setup and give him/her necessary information during a therapy that is performed by the medical apparatus.

Thereby, parameter input is an essential part of such medical equipment. For example, extracorporal blood treatment (ECB) involves the continuous withdrawal of blood from a patient, where the blood is processed within a medical device outside of the patient and is then returned to the patient. Parameters like the ultrafiltration volume, the therapy time and the ultrafiltration rate can be input by a nurse depending on the patient's prescription, and the medical apparatus can then individually perform the therapy for each patient. Furthermore, the therapy can be monitored by the nurse via the user interface. Thereby, parameters like the arterial pressure, the venous pressure, the heparin rate, the dialysate flow, etc. are measured and displayed to the nurse for observation purposes.

Thereby, different people might prefer different information displayed on a screen. Thus, usability and the adaption of graphical user interfaces to the needs and preferences of the users are an issue, since the work of users is better and safer with a medical apparatus that fulfills her/his needs, and such customization becomes a focus area. However, there is a conflict between different user needs and handling problems.

Usually, there are different user needs at different locations and praxises, but this leads to handling problems, if every possible user need is accounted for. These handling problems have been created by the traditional answer how to fulfill the above-mentioned different user needs of different locations and praxises. This traditional way is in fact just packing everything onto the same user interface, which may be necessary by any user, any location and any praxises. However, this often leads to overloaded screens and menu structures of the user interface of an ECB equipment, and resulting handling problems have been reported from the field.

Furthermore, the customization is typically performed by technical staff after equipment installation, and the nurses have to inform the technical staff about the desired customization. Consequently, they have to decide at an early stage what kind of customization they prefer. If their preferences change during operation of the medical apparatus, it should be possible for the nurses to change the customization without contacting the technical staff again.

SUMMARY OF THE INVENTION

The present invention addresses the mentioned usability issue, and it is an objective of the invention to provide a method for easy and clear customization of the user interface of a medical apparatus for extracorporal blood treatment even during therapy. It is another objective of the invention to provide a corresponding medical apparatus for extracorporal blood treatment.

According to aspects of the invention, this objective is achieved by a method having the features of independent claim 1. Advantageous refinements of this method are set forth in dependent claims 2 through 14. The objective is also achieved by a medical apparatus according to claim 15.

The method according to aspects of the invention can be used for customization of a user interface of a microprocessor controlled medical apparatus for extracorporal blood treatment, whereby the medical apparatus comprises a software component driving the user interface on a touch screen of the medical apparatus. The software component has a technical support and maintenance mode and a treatment mode, and at least one target window is displayed on the touch screen during therapy in the treatment mode, whereby such target window shows at least data regarding measured and/or set values of the therapy. Thereby, at least the appearance of one target window is modified by a customization procedure that is performed within the target window in the treatment mode.

Thus, the invention resolves the conflict between customization of a user interface and usability by providing a procedure on the user interface itself, by means of which an acceptable minimum set-up for a specific user need and specific location and praxis can be easily and safely created. Thereby, customization of the user interface means that in a defined though limited way and extent, certain screens, their picture elements, the navigations on the user interface shall be configured by not only the technical staff (typically after equipment installation), but by the nursing staff, too. The customization can take place in the operation room and even during the therapy, whereby a nurse does not have to enter a special user set-up in order to modify the appearance of a current target window, because customization can take place within the particular target window itself.

The design, verification and validation of the user interface covers the maximum set-up of the user interface, i.e. the union of all the potential specific set-up, this way taking a special care of fulfilling the corresponding regulatory requirements. Thereby, measures and/or set values of the therapy can be customized. Measured values are values of the actual arterial pressure, the actual venous pressure, the actual heparin rate during therapy, for example. Set values can be parameters like the ultrafiltration volume, the therapy time and the ultrafiltration rate, for example, that are input by a nurse depending on the patient's prescription. Thus, the values mentioned in this application can be actual values that are measured during therapy by sensors, for example, or parameters that are set by an operator before and/or during therapy.

According to one (separate) aspect of the invention, the customization procedure may modify the selection of values that are displayed in the target window in numerical form in defined positions. Thereby a first value is displayed in a defined position within the target window, and a second value is displayed in this defined position instead of the first value by means of the customization procedure.

According to another (separate) aspect of the invention, the customization procedure may modify the selection of values that are displayed in the target window in graphical form in defined positions. Thereby, a first value is displayed graphically within the target window, and a second value is displayed graphically instead of the first value by means of the customization procedure.

In order to inform the operator of the medical apparatus of customizable positions and values, an indication of selectable second values can be displayed within the target window. Thereby, the indication of selectable second values can permanently be displayed within the target window. This can be advantageous, because the operator can always see all possible parameters. However, the respective window might be overloaded then. Therefore, it can be preferred that the indication of selectable second values is only temporarily displayed within the target window.

The indication of selectable second values can be produced in different ways. For example, menu buttons can be provided, and when an operator pushes a menu button, selectable second values appear within the target window. In one embodiment of the invention, the indication of selectable second values for a defined position is temporarily displayed upon selection of said defined position. Thereby, an operator touches a defined position that he/she wants to modify and a menu of selectable parameters for this position opens within the target window, for example. This menu can be a drop-down menu.

According to a further (separate) aspect of the invention, the customization procedure may be executed by a drag-and-drop operation that involves dragging the indication of one selected value to the defined position on the touch screen. This provides for an easy way of modifying the appearance of a target window, whereby selectable values can be dragged from the frame of the window to the defined position.

Furthermore, the customization procedure can be executed by a selection operation that involves selecting a second value from a menu via the touch screen. Preferably, the selection operation then involves confirming a selected second value via the touch screen. If a customization is confirmed, the modified target window is used for the current therapy.

The target window can be a trend window, a prescription window, a protocol window or information window, for example. Thereby, each target window can comprise customizable and non-customizable data. A trend window graphically shows the trend of one or more particular actual value over the therapy time and allows monitoring the arterial and venous pressure, for example. This trend can be the main screen during therapy, whereby it can be preferred that only one parameter is displayed in this window by means of a graph.

A prescription window may numerically shows actual prescription parameters like the UF volume, the therapy time, the heparin rate, the dialysate flow, etc. A protocol window may contains all dialysis data which are needed to document by the nurse during the whole therapy. For example, the blood pressure of the patient shall be written down in every half hour by the nurse. Thereby, the protocol window may contains the last measured values.

An information window can show a great number of parameters like the arterial and venous pressure, the actual heparin rate, the actual value PBE, etc. in one window. Thereby, an information window can comprise an actual part for displaying actual values, and a history part for displaying the history of values, whereby the history can be displayed graphically in form of several graphs again.

The invention further comprises a medical apparatus for extracorporal blood treatment that is microprocessor controlled and comprises a touch screen and a software component, whereby the software component drives a user interface on the touch screen and has a technical support and maintenance mode and a treatment mode. At least one target window can be displayed by the user interface on the touch screen during therapy in the treatment mode, and such target window can show at least data regarding measured values of the therapy. Furthermore, the medical apparatus comprises means for customization of the user interface with the method according to aspects of the invention.

Additional advantages, special features and practical refinements of the invention can be gleaned from the dependent claims and from the presentation below of preferred embodiments making reference to the figures.

DETAILED DESCRIPTION OF THE PREFERRED EMBODIMENTS

Figure 1:
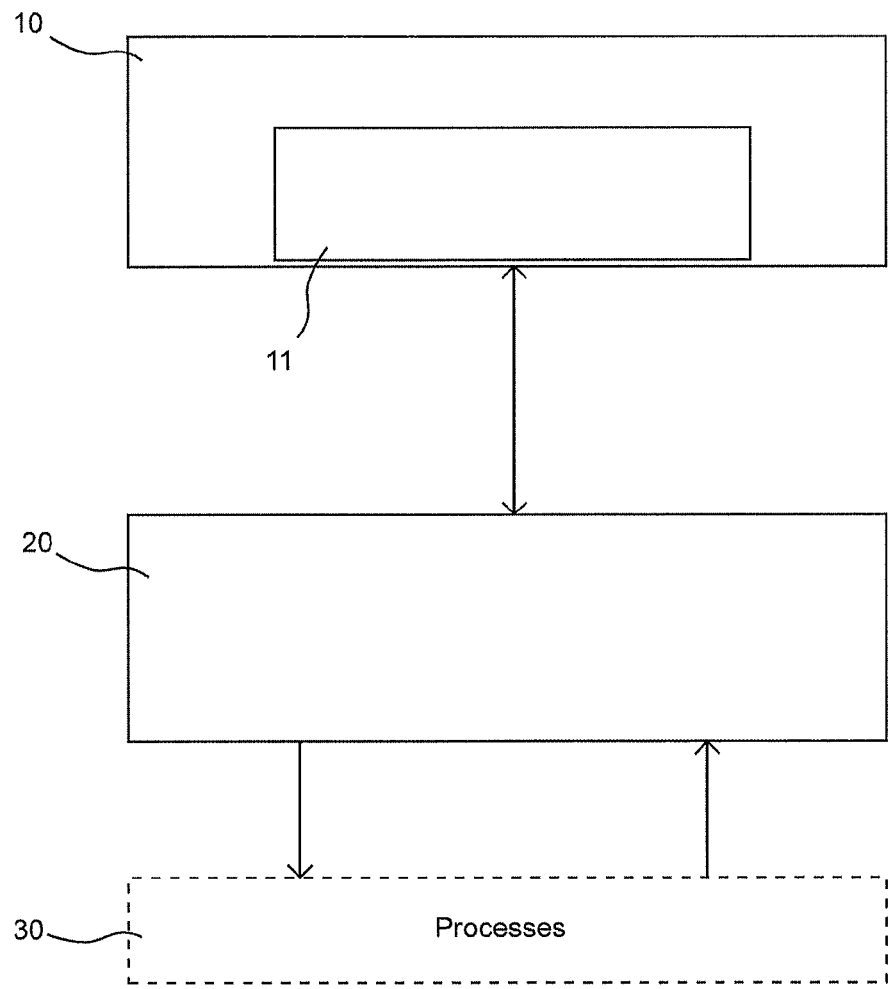
FIG. 1 a schematic illustration of an architecture to implement the method according to the invention.

FIG. 1 shows a diagram depicting the basic features of a system architecture of a microprocessor controlled extracorporal blood treatment device (ECB device). The ECB device comprises at least an extracorporal blood circuit, pumps and sensors (not shown) and a software component 20 that controls processes 30 for performing the therapy functions of the ECB device. The ECB device also comprises a screen 10 on which several target windows 11 can be displayed by the computer user interface of the software component 20 that runs on the main CPU of the ECB device. Preferably, the screen 10 is a touchscreen which allows display and input of information by a user of the ECB device.

The software component 20 has at least two modes. One is the technical support and maintenance mode (TSM) in which technical staff can perform support and maintenance operations. The second mode is the treatment mode in which the therapy is performed by the nursing staff. Thereby, the preparation of the ECB device for therapy and the therapy itself are performed in the treatment mode. In addition to the method for customization of the user interface during the therapy, the technical support and maintenance mode preferably also provides means for customization by the technical staff. Furthermore, system configuration settings before the start of a therapy can be available in the treatment mode, too (user set-up). However, the invention is directed to customization of a user interface in the treatment mode during therapy.

Thereby, the processes 30 and sensors of the ECB device can provide data which is displayed on the user interface during therapy in the treatment mode. This data can be displayed together with other data in so-called target screens or target windows 11, whereby a target window 11 shows at least data regarding measured/actual values of the therapy. Hereby, measured values can be the actual arterial pressure, the actual venous pressure, the actual pressure of the arterial side before the dialyser (PBE/Pressure Blood Entrance), the actual heparin rate, total conductivity or other parameters which are important and to be monitored during therapy. Thereby, the actual values can be displayed in numerical and/or graphical form.

Figure 2A:
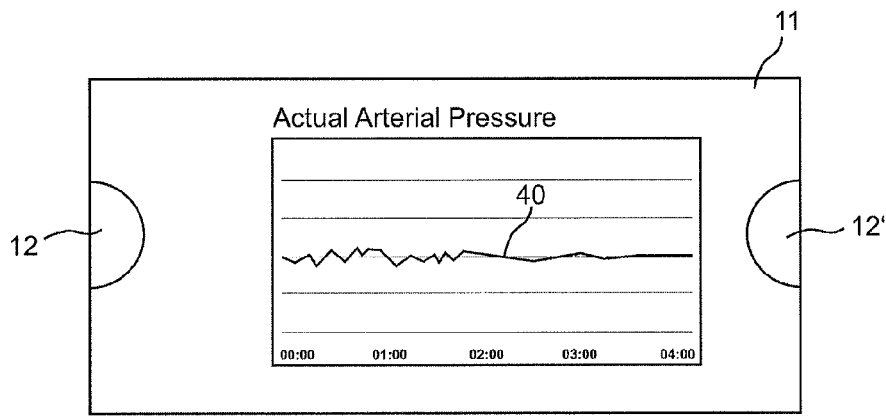
FIG. 2a one embodiment of a trend window before customization.

One example of a customizable target window is a trend window (Trend on Main Screen). This kind of window graphically shows the trend of one or more particular actual value over the therapy time. FIG. 2a shows one embodiment of such trend window that displays the actual arterial pressure over the therapy time in graph 40. The graph 40 is displayed in a defined position within the target window 11, and one or more graphs for different values can be displayed. It is preferred that only one single parameter is graphically displayed in this kind of trend window 11, but the selection of displayed values can be customized by an operator during therapy.

Two menu buttons 12 and 12' are located on both sides of the target window 11 in order to give an operator information about selectable second values. If the left menu button 12 is touched by an operator, for example, two selectable values 41 and 42 are displayed in the left frame region of the target window 11 without overlapping the graph 40. One selectable value is the actual venous pressure (VEN), whereas the other selectable value is the actual value PBE. Preferably, the actual value of each parameter is displayed numerically, too.

Figure 2B:
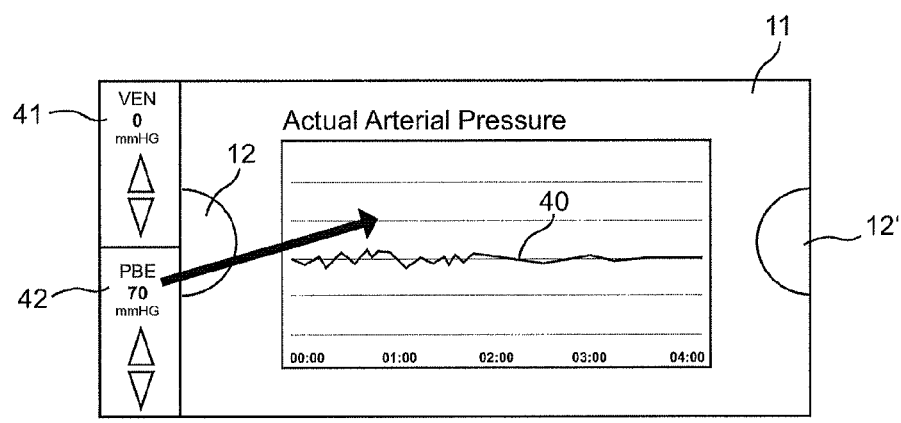
FIG. 2b the trend window according to FIG. 2a during customization.
Figure 2C:
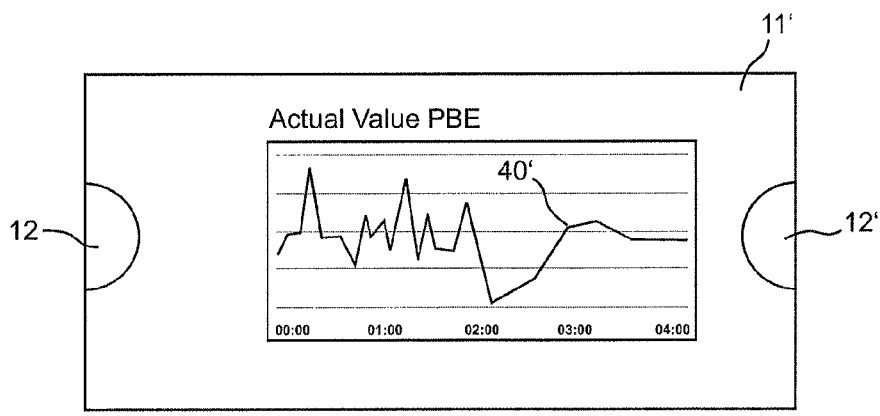
FIG. 2c the trend window according to FIG. 2a after customization.

If an operator now wants to have the trend of the actual value PBE to be displayed in a graph, the operator can perform a customization of the user interface by means of a drag-and-drop operation. Thereby, the operator touches the PBE in the left menu and drags it onto the graph 40. This operation is illustrated by an arrow in FIG. 2b. The graph 40' will then display the actual value PBE instead of the actual arterial pressure, and the selectable values on the left side will disappear again. FIG. 2c shows such customized target window 11'. Consequently, the actual arterial pressure will now be a selectable value, if the operator again wants to customize the target window 11.

Figure 3A:
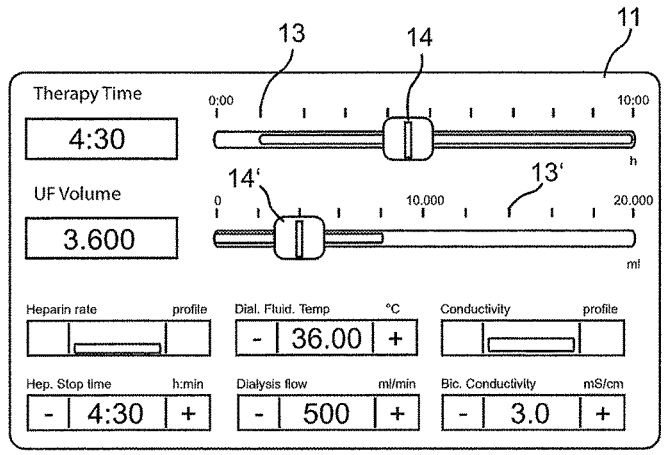
FIG. 3a one embodiment of a prescription window before customization.

Another embodiment of a customizable target window 11 is a prescription window. An example of such prescription window 11 is shown in FIG. 3a. This prescription window 11 shows actual prescription values of the therapy time and the UF volume, for example. These values can be displayed numerically and by means of sliders 14, 14' on a scale 13, 13'. Preferably, these values are non-customizable, but additional values below these scales are customizable. However, in another embodiment of the invention, these values are examples of set values that can be customizable, too.

The customizable values can comprise the heparin rate, the dialysis fluid temperature, the conductivity, the heparin stop time, the dialysate flow and/or the bicarbonate conductivity, for example, and these values are displayed in defined positions within the window 11. Thereby, the actual values are displayed in numerical form. These positions and values might have been set in the TSM mode and/or the user set-up in the treatment mode, but these positions are now customizable during therapy in the treatment mode, too.

If the operator wants to have different values to be displayed in the prescription window 11 or wants to have certain values to be displayed in a different position, the operator can open a menu 43 with selectable values. Thereby, the operator has to indicate which defined position within the window 11 he/she wants to modify. This can be done by touching the defined position. When the user touches the number or the +/− buttons of one of the elements, then the selected value will be edited. So the element can be selected for customization by pressing the label of the element or double clicking the whole element, for example. Upon selection of a defined position/value, a menu with selectable values opens within the window 11. Thereby, the menu can comprise more values than positions are defined in the window 11.

Figure 3B:
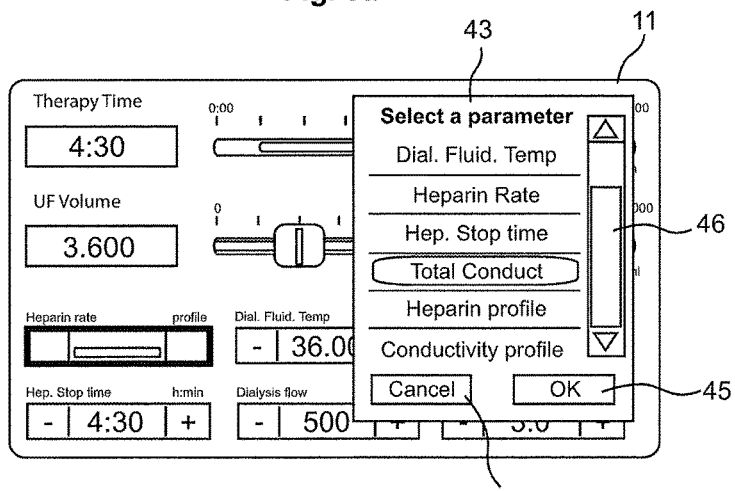
FIG. 3b the prescription window according to FIG. 3a during customization.

In FIG. 3b, the heparin rate has been selected to be customized in the window 11, and this position is highlighted in order to indicate to the operator that customization can be performed. This is illustrated in FIG. 3b by a dark black frame. A menu 43 now shows all parameters that can be selected for the chosen position. Preferably, the menu 43 also comprises a "CANCEL" software button 44 and an "OK" software button 45. The operator can select a value from the menu 43 by touching and thereby highlighting it directly. Alternatively, the operator can move a bar 46 up and down to select a highlighted value. If the operator touches the "OK" software button 45, the chosen position is modified accordingly. If the operator touches the "CANCEL" software button 44, no customization is performed and the menu 43 might be closed.

Figure 3C:
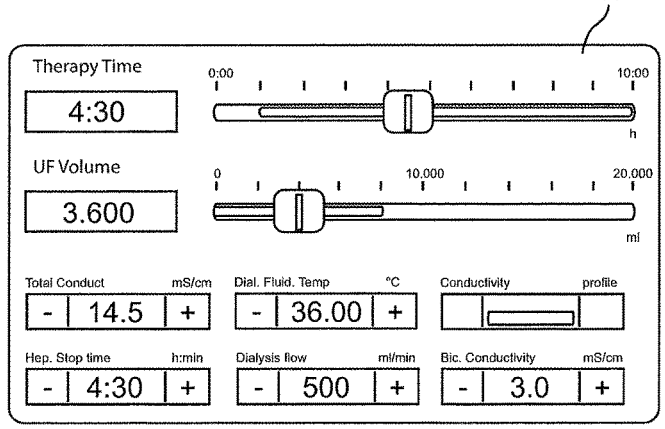
FIG. 3c the prescription window according to FIG. 3a after customization.

In the example of FIG. 3b, the total conductivity has been chosen in menu 43, and FIG. 3c shows the resulting modified prescription window 11' with the total conductivity in the former position of the heparin rate. The heparin rate is not displayed in the prescription window 11' anymore.

Preferably, values and positions can repeatedly be customized during the therapy. Furthermore, a current customization can be retained for the therapy of the next patient. Alternatively, the next therapy can be started with a default set up and the operator can then customize the target windows differently depending on the patient and/or situation.

The invention claimed is:

1. A method for customization of a user interface of a microprocessor controlled medical apparatus for extracorporal blood treatment, whereby the medical apparatus comprises a software component driving the user interface on a touch screen of the medical apparatus, and the software component has a technical support and maintenance mode and a treatment mode in which a patient therapy is taking place, and at least one target window is displayed on the touch screen during the patient therapy in the treatment mode, whereby said target window displays at least one of measured parameters or set parameters of the therapy, and at least the appearance of one target window is modified by a customization procedure that is performed within the target window during the treatment mode to modify selection and position of parameters, the method comprising the steps of:

displaying a plurality of defined positions within the target window during the patient therapy, wherein at least one measured parameter or set parameter is displayed in the target window in graphical form in a first of the plurality of displayed defined positions as a first parameter;

identifying a first touch selection within the first of the displayed defined positions; displaying, during the patient therapy, a menu within the target window including a plurality of selectable parameters in response to identifying the first touch selection; receiving a second touch selection of one of the plurality of the displayed selectable parameters; and positioning, during the patient therapy, the one of the plurality of selectable parameters in the first of the displayed defined positions as a second parameter, such that the first parameter is displayed graphically within the target window in the first of the displayed defined positions, and the second parameter is subsequently displayed either numerically or graphically in the first of the displayed defined positions instead of the first parameter.

2. The method according to claim 1, wherein at least one measured parameter or set parameter is displayed in the target window in numerical form in at least one of the displayed defined positions.

3. The method according to claim 1, wherein the menu within the target window including the plurality of displayed selectable parameters is temporarily displayed within the target window.

4. The method according to claim 3, wherein the menu within the target window including the plurality of displayed selectable parameters for a defined position is temporarily displayed upon the first touch selection within the first of the displayed defined positions.

5. The method according to claim 1, wherein the second touch selection is executed by a drag-and-drop operation comprising dragging the one of the plurality of displayed selectable parameters to the first of the plurality of displayed defined positions on the touch screen.

6. The method according to claim 1, wherein the method further comprises confirming, during the patient therapy, the second parameter via the touch screen with a confirmation touch selection.

7. The method according to claim 1, wherein the target window is a trend window, a prescription window, a protocol window or information window.

8. The method according to claim 1, wherein the target window comprises customizable and non-customizable data.

9. The method according to claim 1, wherein the first and second touch selections are responsive to preferences of a first operator during the patient therapy; and the method further comprising the steps of:

identifying a third touch selection within the first of the displayed defined positions for a second operator during the patient therapy;

displaying the menu within the target window including the plurality of selectable parameters during the patient therapy; and receiving a fourth touch selection of another one of the plurality of the displayed selectable parameters during the patient therapy; and positioning the other one of the plurality of displayed selectable parameters in the first of the defined positions during the patient therapy.

10. The method according to claim 1, wherein the method further comprises the steps of:

identifying a third touch selection within a second of the displayed defined positions during the patient therapy;

displaying the menu within the target window including the plurality of selectable parameters during the patient therapy;

receiving a fourth touch selection of another of the plurality of the displayed selectable parameters during the patient therapy; and positioning the other of the plurality of selectable parameters in the second of the displayed defined positions during the patient therapy.

11. A medical apparatus for extracorporal blood treatment that is microprocessor controlled and comprises a touch screen and a software component, whereby the software component drives a user interface on the touch screen and has the technical support and maintenance mode and the treatment mode in which the patient therapy is taking place, and at least one target window can be displayed by the user interface on the touch screen during the patient therapy in the treatment mode, whereby said target window can display at least one of measured parameters or set parameters of the patient therapy, and the medical apparatus comprises means for customization of the user interface in real-time during the patient therapy with the method according to one of claims 2, 3 to 5, 6 to 8, 9, and 10, the means for customization of the user interface including:

a user interface driven by the software component configured to:

display, during the patient therapy, a plurality of defined positions within the target window of the user interface, wherein at least one measured parameter or set parameter is displayed in the target window in graphical form in a first of the plurality of displayed defined positions as a first parameter;

identify a first touch selection by a user within the first of the displayed defined positions;

display, during the patient therapy in response to the identified first touch selection, a menu within the target window including a plurality of selectable parameters;

receive a second touch selection by the user of one of the plurality of the displayed selectable parameters; and position, during the patient therapy, the second touch-selected one of the plurality of selectable parameters in the first of the displayed defined positions as second parameter, such that the first parameter is displayed graphically within the target window in the first of the displayed defined positions, and the second parameter is subsequently displayed either numerically or graphically in the first of the displayed defined positions instead of the first parameter.

* * * * *